US009188434B2

(12) United States Patent
Xu et al.

(10) Patent No.: US 9,188,434 B2
(45) Date of Patent: Nov. 17, 2015

(54) BACKSIDE ALIGNMENT APPARATUS AND METHOD

(75) Inventors: Bing Xu, Shanghai (CN); Yuefei Chen, Shanghai (CN); Xiang Jia, Shanghai (CN); Xiaoqing Yang, Shanghai (CN)

(73) Assignee: SHANGHAI MICRO ELECTRONICS EQUIPMENT CO., LTD., Shanghai (CN)

( * ) Notice: Subject to any disclaimer, the term of this patent is extended or adjusted under 35 U.S.C. 154(b) by 174 days.

(21) Appl. No.: 13/976,376

(22) PCT Filed: Dec. 20, 2011

(86) PCT No.: PCT/CN2011/084264
§ 371 (c)(1),
(2), (4) Date: Jun. 26, 2013

(87) PCT Pub. No.: WO2012/089043
PCT Pub. Date: Jul. 5, 2012

(65) Prior Publication Data
US 2013/0271750 A1    Oct. 17, 2013

(30) Foreign Application Priority Data
Dec. 28, 2010  (CN) .......................... 2010 1 0619055

(51) Int. Cl.
*G01B 11/00*   (2006.01)
*G01B 11/26*   (2006.01)
(Continued)

(52) U.S. Cl.
CPC ................ *G01B 11/26* (2013.01); *G01N 21/35* (2013.01); *G03F 9/7015* (2013.01); *G03F 9/7084* (2013.01); *G03F 9/7088* (2013.01)

(58) Field of Classification Search
CPC ...... G01B 11/26; G01N 21/35; G03F 9/7015; G03F 9/7084; G03F 9/7088
See application file for complete search history.

(56) References Cited

U.S. PATENT DOCUMENTS 4,452,526 A * 6/1984 Johannsmeier et al. ........ 355/43
4,475,122 A * 10/1984 Green ............................ 348/87
(Continued)

FOREIGN PATENT DOCUMENTS

CN    101382743 A    3/2009
CN    101436006      5/2009
(Continued)

OTHER PUBLICATIONS

European search report from cooresponding application No. PCT/CN2011084264 mailed May 12, 2014, 6 pages.
(Continued)

*Primary Examiner* — Kara E Geisel
(74) *Attorney, Agent, or Firm* — Muncy, Geissler, Olds & Lowe, P.C.

(57) ABSTRACT

A backside alignment apparatus and method for determining a position relationship between a substrate (6) and a workpiece stage (24). The backside alignment apparatus includes: an illumination apparatus (1) for emanating infrared light; a workpiece stage assembly (2) for supporting and moving the substrate (6); an imaging apparatus (3) for detecting alignment marks and calculating positions of the alignment marks, the alignment marks including a reference plate alignment mark (41) and a backside alignment mark (20); and a reference plate assembly (4) for setting up a relationship between position coordinates of the imaging apparatus (3) and the workpiece stage assembly (2). The illumination apparatus (1) and the imaging apparatus (3) are able to illuminate and align different alignment marks using only one set of illumination apparatus.

12 Claims, 6 Drawing Sheets

(51) Int. Cl.
*G03F 9/00* (2006.01)
*G01N 21/35* (2014.01)

(56) References Cited

U.S. PATENT DOCUMENTS

| | | | |
|---|---|---|---|
| 5,843,831 A * | 12/1998 | Chung et al. | 438/401 |
| 6,198,535 B1 | 3/2001 | Hu et al. | |
| 6,525,805 B2 | 2/2003 | Heinle | |
| 6,676,878 B2 * | 1/2004 | O'Brien et al. | 264/400 |
| 6,768,539 B2 | 7/2004 | Gui et al. | |
| 7,751,067 B1 * | 7/2010 | True et al. | 356/614 |
| 2004/0201833 A1 | 10/2004 | Gui et al. | |
| 2006/0115956 A1 | 6/2006 | Raval et al. | |

FOREIGN PATENT DOCUMENTS

| | | |
|---|---|---|
| CN | 101436006 A | 5/2009 |
| CN | 101685275 | 3/2010 |
| CN | 101685275 A | 3/2010 |
| JP | 2000-299276 A | 10/2000 |

OTHER PUBLICATIONS

Chinese search report from cooresponding application No. CN201010619055.2 mailed Aug. 30, 2013, 6 pages.
Chinese search report from cooresponding application No. CN201010619055.2 mailed Apr. 21, 2014, 3 pages.
Chinese search report from cooresponding application No. CN201010619055.2 mailed Sep. 29, 2014, 3 pages.

* cited by examiner

BACKSIDE ALIGNMENT APPARATUS AND METHOD

TECHNICAL FIELD

This invention relates in general to integrated circuit manufacturing devices, and more particularly, to an apparatus and method for backside alignment in a semiconductor lithography device.

BACKGROUND

With the continuous improvement of our living standards and the increasing development of semiconductor technologies, in the future semiconductor market, there will be an increasing demand for the level-up of intelligence and miniaturization of semiconductor packing devices. For example, digital products, such as digital cameras, mobile phones, PDAs and the like will be required to have a smaller size for ease of carrying, diverse functionalities and a high price-performance. In order to meet the demand for the development of intelligence and miniaturization of semiconductor packing devices, there arises a need for multi-chip packaging (MCP) solutions to package two or more planar devices in a stacking-and-connecting way at a wafer level. Such packaging method is also known as three-dimensional (3D) packaging. Currently, there are three major ways to achieve 3D packaging, namely wire bonding, flip chip bonding and through silicon via (TSV) bonding. Among these bonding methods, TSV bonding is considered as one of the most potential and promising 3D packaging methods, because it has many advantages such as a smaller length and a higher density of bonding leads, a smaller package area and non-significant increase of package cost with the increase in the number of packaged chips, compared with the relatively conventional wire bonding method. In the TSV bonding method, fine vias are formed through each semiconductor silicon chip, namely extending from the frontside to the backside of the semiconductor silicon chip, and then the stacked silicon chips are electrically connected to one another. As semiconductor silicon chips are bonded in a three dimensional and vertical way, bonding leads arranged between the silicon chips can be greatly shortened and a final device can be significantly improved in terms of volume, performance and signal access and transmission speed.

As the TSV bonding method requires exposure to the backside of a wafer, relevant semiconductor lithography devices are required to be equipped with a backside alignment apparatus which uses a pattern formed on a frontside (or a top surface) of the wafer as a reference mark for a backside (or a bottom surface) of the wafer to determine a deviation between positions of the pattern formed on the frontside and a pattern to be exposed on the backside of the wafer. Thus, measuring precision of the backside alignment apparatus critically determines the overlay errors between patterns formed on the frontside and backside.

Currently, there are mainly two methods for carrying out backside alignment of a wafer, namely visual light measuring method and infrared light measuring method. In a visual light measuring method, a light-path turning device and an imaging device are arranged on opposite sides under a wafer stage for illuminating and imaging a backside reference mark of the wafer using a visual light. While in an infrared light measuring method, a backside reference mark of the wafer is illuminated and imaged by using the wafer penetrating property of the infrared light. However, the above two methods for carrying out backside alignment for a wafer each have advantages and disadvantages in configuration.

U.S. Pat. Nos. 6,525,805B and 6,768,539B respectively disclose a typical backside alignment apparatus, which uses an off-axis alignment apparatus to achieve wafer backside alignment with visual light measuring method. However, as too many illumination devices for illuminating backside alignment marks are incorporated in this apparatus, each backside alignment mark corresponding to a set of illumination devices, it is complicated and expensive to assemble these illumination devices together. Moreover, its design of arranging the illumination devices under a wafer stage leads to a high complexity and processing cost in structure design of the wafer stage. Furthermore, as each of the backside alignment marks must be positioned within an illumination field of its associated illumination devices, the apparatus has poor process adaptation.

Moreover, U.S. Pat. No. 6,525,805B also discloses a backside alignment apparatus using infrared light measuring method. In this apparatus, near-infrared light sources are arranged at different positions within the wafer stage for illuminating backside alignment marks of the wafer, and a near-infrared imaging device is disposed above the wafer for imaging the alignment marks. As illumination devices for illuminating backside marks of the wafer are arranged within the wafer stage, the structure design and assembly of the wafer stage are complicated and may have a high processing cost; moreover, the structure design may be restricted by the overall alignment accuracy of the wafer and space size of the wafer stage. Furthermore, alignment marks need to be formed at predetermined positions to co-work with the backside mark illumination devices, thus increasing process steps and complexity and leading to a poor process adaptation.

SUMMARY OF THE INVENTION

The present invention overcomes the foregoing drawbacks of the conventional art by presenting a backside alignment apparatus and method, which are simpler in configuration and able to overall reduce design and processing complexities for integrated circuit fabrication equipment.

To achieve the above objectives, the present invention discloses a backside alignment apparatus for determining a relationship between relative positions of a substrate and a workpiece stage. The backside alignment apparatus comprises: a radiation source for emanating infrared light; a workpiece stage assembly for supporting and moving the substrate; an imaging apparatus for detecting alignment marks and calculating positions of the alignment marks; and a reference plate assembly for setting up a relationship between position coordinates of the imaging apparatus and the workpiece stage assembly. In this invention, illumination and alignment of multiple alignment marks, including both a reference plate alignment mark and backside alignment mark(s), can be achieved only using one set of radiation source and imaging apparatus.

Further, the workpiece stage assembly may include at least three apertures for the infrared light to pass through.

Further, the backside alignment apparatus may further comprise an illumination apparatus.

Further, the illumination apparatus may be disposed above the workpiece stage assembly, and in this case the illumination apparatus includes an optical fiber and an illumination lens group. Moreover, the illumination apparatus may also be disposed under the workpiece stage assembly, and in this case it includes an optical fiber, an illumination lens group and an illuminating reflection mirror.

Further, the workpiece stage assembly may include a workpiece stage and a base under the workpiece stage, and the workpiece stage is able to move in at least three degrees of freedom with respect to the base. Moreover, the workpiece stage may further include a chuck which is made of glass or a material with a high transmittance for infrared light and disposed on the workpiece stage. In addition, the at least three apertures include one base aperture and two workpiece stage apertures.

Further, the imaging apparatus may be disposed right above one of the apertures in the workpiece stage assembly, and in this case the imaging apparatus includes an imaging lens group, an imaging detector and an image processing system. Moreover, the imaging apparatus may also be disposed right under one of the apertures in the workpiece stage assembly, and in this case it includes an imaging lens group, an illuminating reflection mirror, an imaging detector and an image processing system. In addition, the imaging detector may be a charge-coupled device (CCD) detector, a complementary metal-oxide-semiconductor (CMOS) detector, or an indium-gallium-arsenide (InGaAs) detector.

Further, the reference plate assembly may include a reference plate, a reference plate alignment mark and a frame. Additionally, the reference plate alignment mark is disposed on a bottom surface of the reference plate. Moreover, the reference plate is fixed on the frame and the reference plate alignment mark is leveling with the backside alignment marks. In addition, the frame is formed of glass or a material with a high transmittance for infrared light. The reference plate assembly may be disposed either on the workpiece stage or on the chuck.

Further, positions, the number and sizes of apertures formed in the workpiece stage may depend on alignment accuracy and the size of a single chip.

The present invention also discloses a backside alignment method for determining a relationship between relative positions of the substrate and the workpiece stage. The method comprises: a) moving the reference plate alignment mark into an imaging field of the imaging apparatus and acquiring a first position information indicating a relationship between position coordinates of the imaging apparatus and the workpiece stage; b) moving each of the at least one backside alignment mark into the imaging field of the imaging apparatus and acquiring a second position information indicating a relationship between position coordinates of the substrate and the imaging apparatus; and c) determining a relationship between positions of the substrate and the workpiece stage based on the first and second position information.

In this method, the step a) may include: a1) moving the workpiece stage to a desired location such that the reference plate alignment mark is located within an imaging field of the imaging apparatus; a2) determining, using the image processing system, whether the reference plate alignment mark is within the imaging detector, and if the reference plate alignment mark is within the imaging detector, then calculating a position of the reference plate alignment mark on a target plane of the imaging detector using the image processing system and recording a horizontal position of the workpiece stage; and a3) if the reference plate alignment mark is not within the imaging detector, then moving the workpiece stage, by a predetermined distance, into a next search location; if the next search location is out of a predetermined search range, then ending the search; and if the reference plate alignment mark is captured within the predetermined search range, then repeating the step a2).

Moreover, the step b) may include: b1) moving the workpiece stage to a desired location such that one of the at least one backside alignment mark is located within an imaging field of the imaging apparatus; b2) determining, using the image processing system, whether the backside alignment mark is within the imaging detector, and if the backside alignment mark is within the imaging detector, then calculating a position of the backside alignment mark on a target plane of the imaging detector using the image processing system and recording a horizontal position of the workpiece stage; b3) if the backside alignment mark is not within the imaging detector, then moving the workpiece stage, by a predetermined distance, into a next search location; if the next search location is out of a predetermined search range, then ending the search; and if the backside alignment mark is captured within the predetermined search range, then repeating the step b2); and determining whether positions, on a target plane of the imaging detector, of all of the at least one backside alignment mark have been calculated, if not, then repeating the steps b1), b2) and b3).

Furthermore, the step c) may include: c1) calculating a relationship between position coordinates of the imaging apparatus and the workpiece stage; c2) calculating a relationship between position coordinates of the substrate and the imaging apparatus; and c3) obtaining a relationship between relative positions of the substrate and the workpiece stage.

The present invention has differences with and advantages over the prior art as follows: as only one set of illumination apparatus is used, complexity in the design and assembly of illumination apparatus can be reduced and the development costs can be hence lowered; as the illumination apparatus can be disposed within, above or under the marble workpiece stage, coupling between physical interfaces of the illumination apparatus and the workpiece stage assembly can be reduced; also, complexity in the structure design and assembly of the workpiece stage, and processing cost of the workpiece stage can be lowered; and the enabling of moving the workpiece stage to search a backside alignment mark in a certain range when it is not found within an imaging field of the image apparatus can improve the process adaptation of the backside alignment apparatus to the backside alignment marks.

BRIEF DESCRIPTION OF THE DRAWINGS

To provide a more complete understanding of the present invention and its advantages, reference is made to the following detailed description on example embodiments, taken in conjunction with the accompanying drawings, in which.

DETAILED DESCRIPTION

Several exemplary embodiments of the present invention will be described below with reference to the accompanying drawings.

Figure 1:
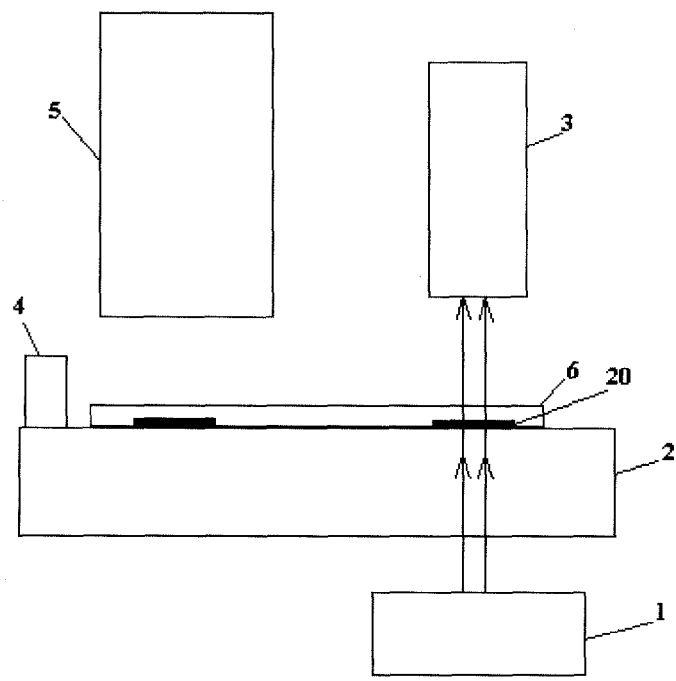
FIG. 1 is a schematic diagram illustrating a backside alignment apparatus embodying the present invention.

The present invention provides a backside alignment apparatus and method for use in integrated circuit fabrication equipments. A schematic diagram illustrating such a backside alignment apparatus is shown in FIG. 1, wherein 5 is a projection objective of an integrated circuit fabrication equipment, which may be a refractive projection objective, a reflective projection objective, or a catadioptric projection objective according to the type of the device being produced; 1 is an illumination apparatus of the backside alignment apparatus according to the present invention, which is configured to provide infrared light illumination; and 6 is a substrate which may be made of silicon, glass or other materials according to the type of device being produced. The substrate 6 is disposed on a workpiece stage assembly 2 which can move in at least three degrees of freedom. Infrared light emanated from the illumination apparatus 1 passes through both the workpiece stage assembly 2 and a backside alignment mark 20 and enters an imaging apparatus 3. Moreover, in this invention, a reference plate assembly 4 is provided for setting up a relationship between position coordinates of the imaging apparatus 3 and the workpiece stage assembly 2.

Figure 2:
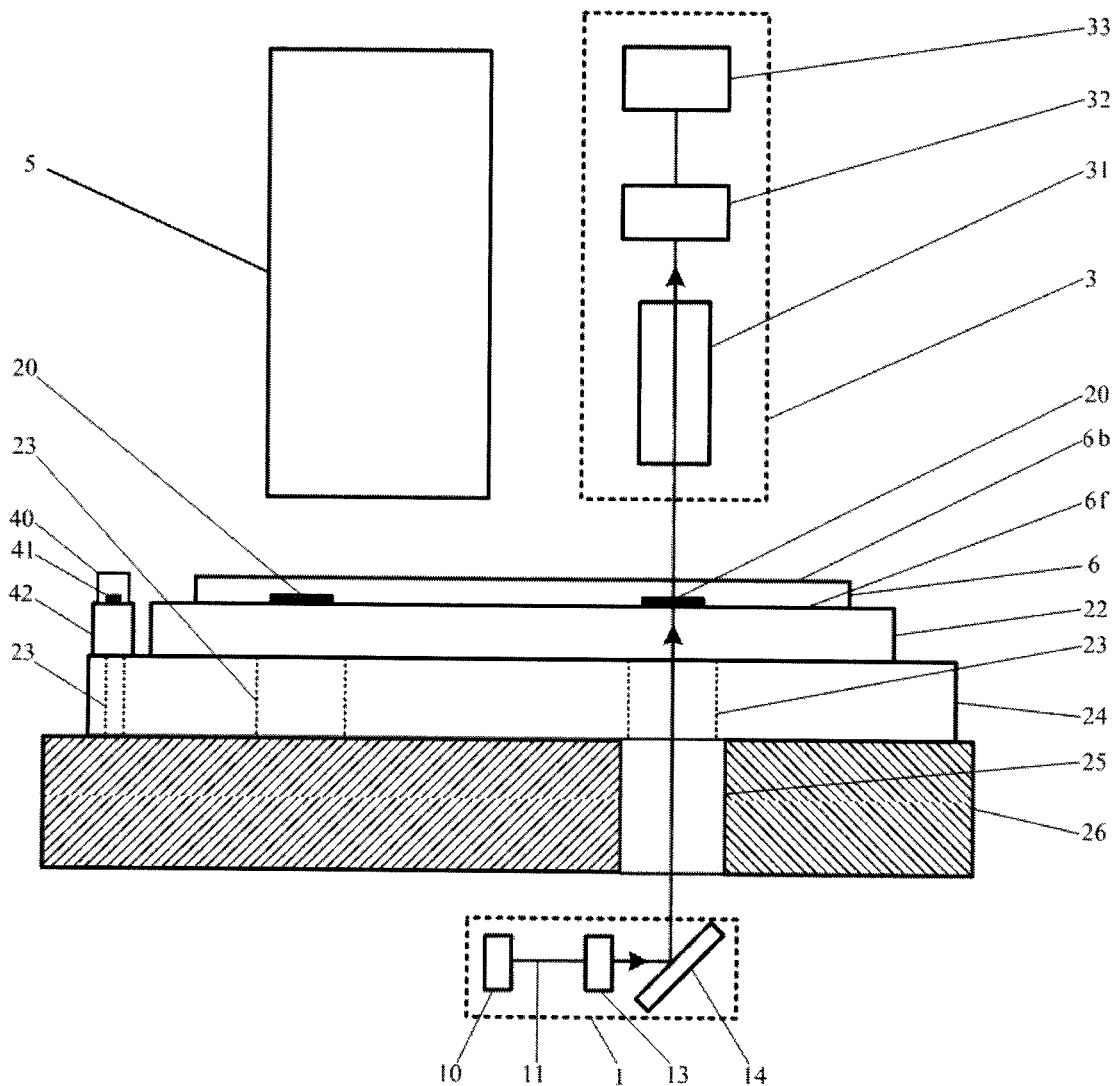
FIG. 2 is a detailed schematic diagram illustrating a backside alignment apparatus according to a first embodiment of the present invention.

FIG. 2 is a schematic illustration of the backside alignment apparatus according to a first embodiment of the present invention. As illustrated, the backside alignment apparatus comprises: an illumination apparatus 1, a workpiece stage assembly 2, an imaging apparatus 3, and a reference plate assembly 4 configured to determine a relationship between positions of a substrate 6 and the workpiece stage assembly 2 by using backside alignment mark(s) 20 formed on the substrate 6.

Referring to FIG. 2, the illumination apparatus 1 successively includes an infrared light source 10, an infrared illumination optical fiber 11, an illumination lens group 13 and an illuminating reflection mirror 14, and is configured to provide uniform illumination for a reference plate alignment mark 41 and backside alignment mark(s) 20 of the substrate 6. The illumination apparatus 1 may have a structure of a Kohler illumination system. Details about the Kohler illumination system can be obtained by referring to the prior art.

The workpiece stage assembly 2 at least includes a workpiece stage 24 with multiple degrees of freedom and a marble base 26. The workpiece stage 24 with multiple degrees of freedom can move in at least three degrees of freedom, and more preferably, it can move in six degrees of freedom. In this case, the six degree-of-freedom workpiece stage 24 is configured mainly to support the substrate 6 and enable the substrate 6 to move in six degrees of freedom. Moreover, the six degree-of-freedom workpiece stage 24 may be disposed on the marble base 26. In this embodiment, the substrate 6 is a silicon substrate as an example and the backside alignment marks 20 are formed on the substrate 6. In addition, in order to fix the substrate 6 more firmly, the substrate 6 is typically disposed on the workpiece stage 24 using a chuck 22 which is arranged at the same level with the backside alignment marks 20 and mounted on a top surface of the workpiece stage 24. Furthermore, the chuck 22 may be formed of glass or a material with a high transmittance for infrared light.

The six degree-of-freedom workpiece stage 24 may include two or more workpiece stage apertures 23 formed in it, including one workpiece stage aperture 23 formed right under the reference plate assembly 4 and the rest of the workpiece stage apertures 23 each formed right under a corresponding backside alignment mark 20, thereby allowing infrared light emanated from the illumination apparatus 1 to pass through the workpiece stage apertures 23 and the chuck 22 and uniformly illuminate the backside alignment mark(s) 20 and the reference plate alignment mark 41. Positions, the number and sizes of the workpiece stage apertures 23 are dependent on alignment accuracy and the size of a single chip.

Similarly, the marble base 26 may also include a marble aperture 25, i.e. a base aperture for allowing infrared light emanated from the illumination apparatus 1 to pass through the marble base 26. The marble aperture 25 is positioned right above the illumination apparatus 1 and right under the imaging apparatus 3 and size of the marble aperture 25 is dependent both on the size of an illumination field of the illumination apparatus 1 and the size of a search range for the backside alignment mark(s) 20.

The reference plate assembly 4 may include a reference plate 40, the reference plate alignment mark 41 and a reference plate frame 42 and is configured to set up a relationship between position coordinates of the imaging apparatus and the workpiece stage. The reference plate alignment mark 41 is positioned on a bottom surface of the reference plate 40 and arranged at the same level with the backside alignment mark(s) 20. In addition, the reference plate 40 may be fixed on the frame 42 and the frame 42 may be formed of glass or a material with a high transmittance for infrared light for allowing the infrared light emanated from the illumination apparatus 1 to pass through the frame 42 and illuminate the reference plate alignment mark 41.

The reference plate assembly 4 may be either fixed on the six degree-of-freedom workpiece stage 24 or directly disposed on the chuck 22, such that its position in each of the six degrees of freedom can be adjusted according to the movement of the workpiece stage 24. In contrast, as the illumination apparatus 1 is disposed under the workpiece stage assembly 2, its position will not be affected by movement of the workpiece stage 24.

Moreover, as the imaging apparatus 3 is disposed above the workpiece stage assembly 2, its position is not affected by movement of the workpiece stage 24. The imaging apparatus 3 may include an infrared imaging lens group 31, an infrared imaging detector 32 and an image processing system 33 and is configured to form clear images of the backside alignment mark(s) 20 and the reference plate alignment mark 41 on a target plane of the infrared imaging detector 32 and calculate positions of these alignment marks. Additionally, the infrared imaging detector 32 is configured to receive images of the reference plate alignment mark 41 and the backside alignment mark(s) 20 generated by the infrared imaging lens group 31. Moreover, the infrared imaging detector 32 may be a charge-coupled device (CCD) detector, a complementary metal-oxide-semiconductor (CMOS) detector, or an indium-gallium-arsenide (InGaAs) detector.

In this design, infrared light emitted from the infrared light source 10 successively passes through the infrared illumination optical fiber 11, the illumination lens group 13, the illuminating reflection mirror 14, the marble aperture 25, the workpiece stage aperture 23 and the chuck 22, reaches the reference plate alignment mark 41 or a backside alignment mark 20 and thus uniformly illuminates the mark. Moreover, a backside alignment imaging process may start from the reference plate alignment mark 41 or a backside alignment mark 20, successively pass through the reference plate 40 or substrate 6, the infrared imaging lens group 31, the infrared imaging detector 32 and reach the image processing system 33. In this process, clear images of the reference plate alignment mark 41 and/or the backside alignment mark(s) 20 can be formed on the infrared imaging detector 32, and the image processing system 33 can acquire positions of the reference plate alignment mark 41 and/or the backside alignment mark(s) 20 on the target plane of the infrared imaging detector 32.

Figure 3:
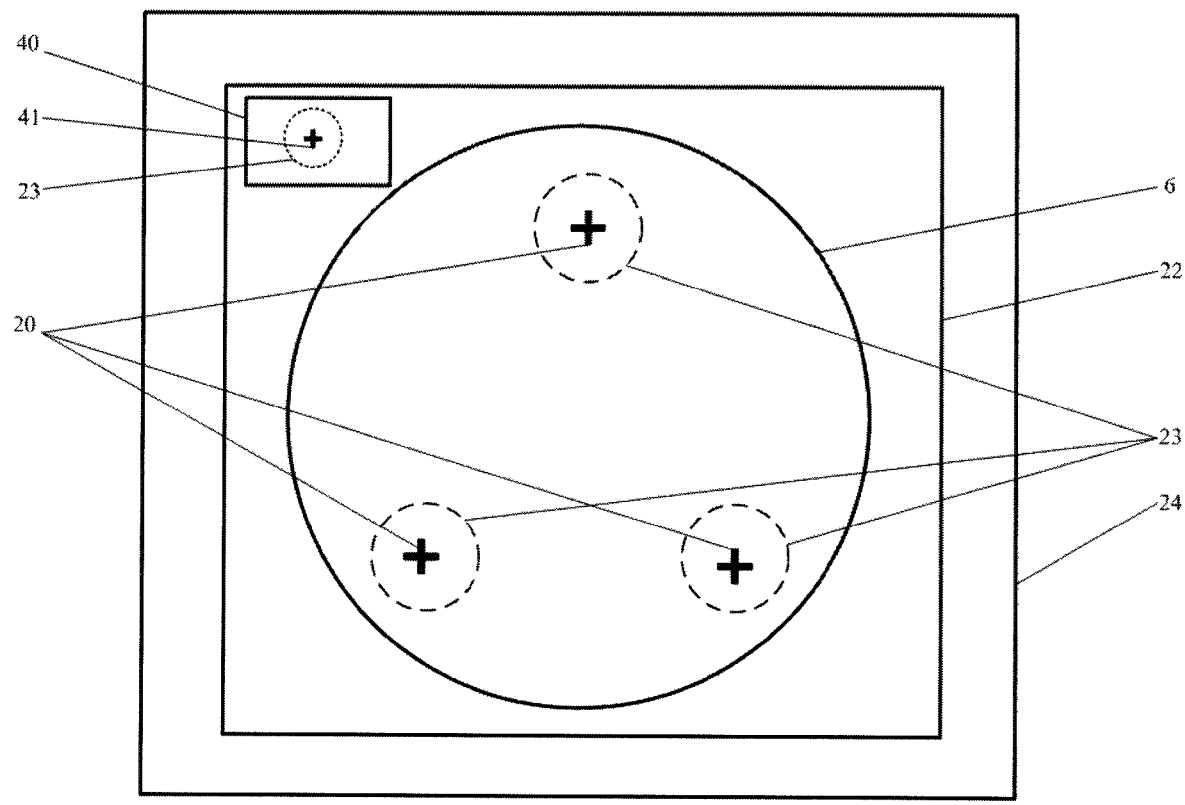
FIG. 3 is a schematic diagram illustrating the configuration of an illumination apparatus of the backside alignment apparatus embodying the present invention.

FIG. 3 schematically illustrates the configuration of an illumination apparatus of the backside alignment apparatus of the present invention. With reference to FIG. 1, the reference plate assembly 4 is arranged at a left upper corner of the six degree-of-freedom workpiece stage 24. In actual arrangement, the reference plate assembly 4 may be arranged at any corner of the workpiece stage 24. In another embodiment, the reference plate assembly 4 may be directed mounted on the chuck 22. Moreover, while the reference plate alignment mark 41 and the backside alignment marks 20 are illustrated as crosses "+" in the figures, persons skilled in the art will recognize that in practical operations different marks can also be used as the reference plate alignment mark 41 or the backside alignment marks 20 according to different alignment accuracies and requirements. As illustrate, in this embodiment, three backside alignment marks 20 and correspondingly three workpiece stage apertures 23 are adopted. Furthermore, each of the workpiece stage apertures 23 has a size that is greater than both an illumination field and a search range associated with the reference plate alignment mark 41 and the backside alignment marks 20.

Figure 4:
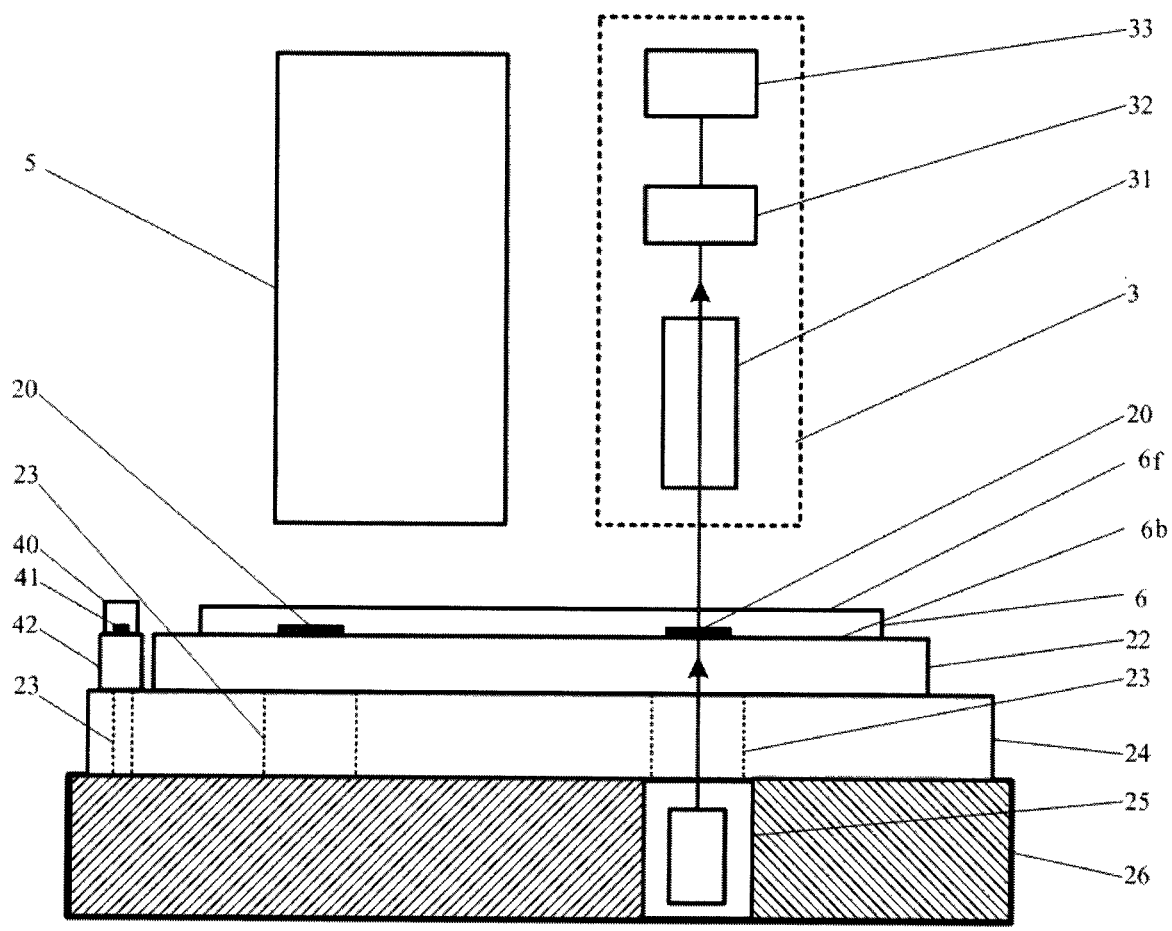
FIG. 4 is a detailed schematic diagram illustrating a backside alignment apparatus according to a second embodiment of the present invention.

FIG. 4 is a detailed schematic diagram illustrating a backside alignment apparatus according to a second embodiment of the present invention. In this embodiment, in order to obtain a backside alignment apparatus with a simpler structure so as to reduce coupling between physical interfaces of the illumination apparatus and the workpiece stage assembly, and thus lower complexity in the structure design and assembly of the workpiece stage as well as processing costs of the lithography equipment, an infrared light source 25 for uniformly illuminating the reference plate alignment mark 41 and the backside alignment mark(s) 20 is embedded within the marble workpiece stage as a replacement of the illumination apparatus 1 of the first embodiment. Compared with the first embodiment, the backside alignment apparatus in this embodiment uses a much smaller number of optical members and thus has a simpler structure and a lower cost.

Figure 5:
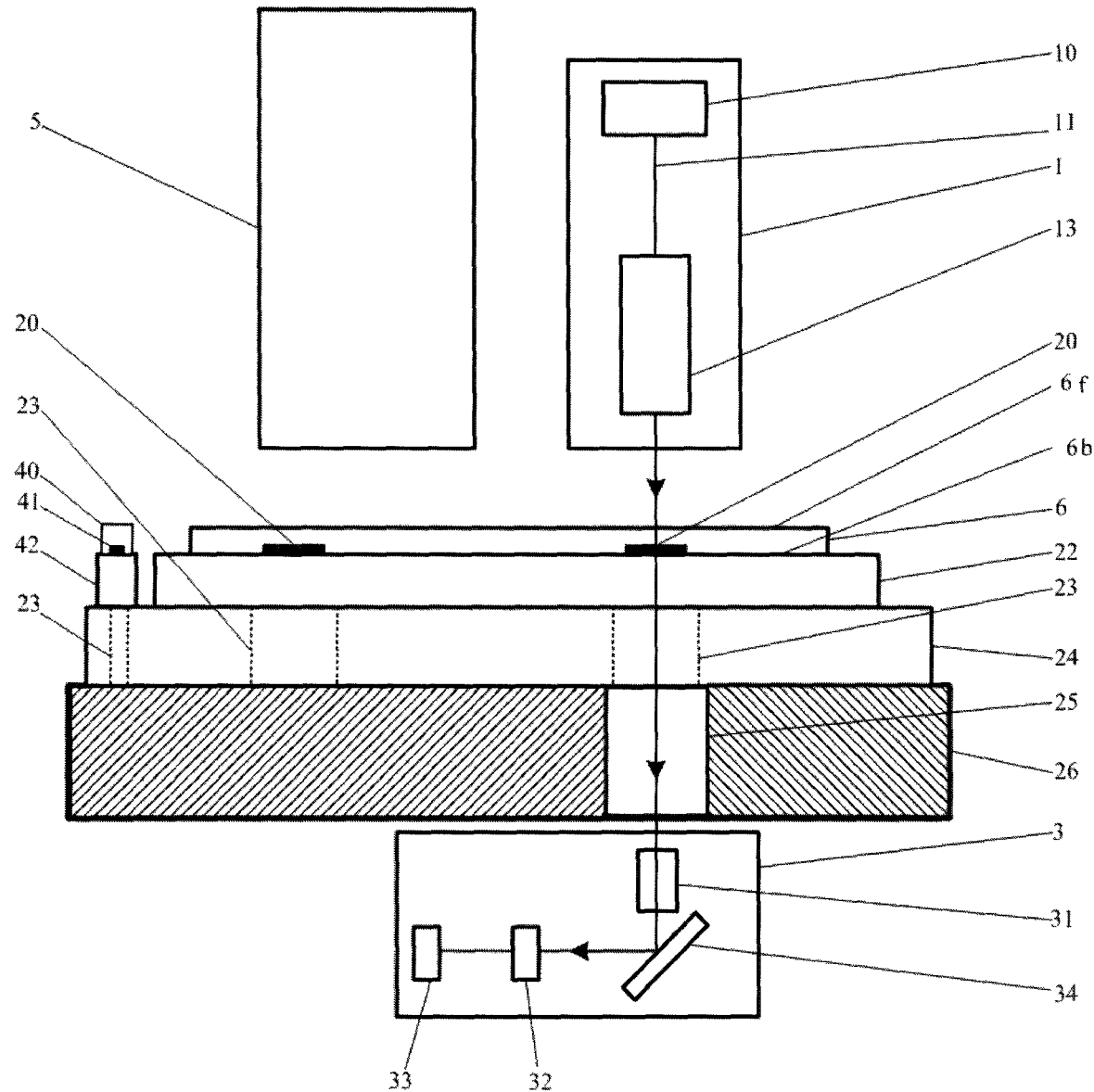
FIG. 5 is a detailed schematic diagram illustrating a backside alignment apparatus according to a third embodiment of the present invention.

FIG. 5 is a detailed schematic diagram illustrating a backside alignment apparatus according to a third embodiment of the present invention. With reference to FIG. 1, in this embodiment, a backside alignment apparatus comprises: an illumination apparatus 1, a workpiece stage assembly 2, an imaging apparatus 3, and a reference plate assembly 4 configured to determine a relationship between positions of a substrate 6 and the workpiece stage assembly 2 by using backside alignment mark(s) 20 formed on the substrate 6. The illumination apparatus 1 may be disposed above the substrate 6 whilst the imaging apparatus 3 is disposed under the substrate 6. Additionally, the illumination apparatus 1 may successively include an infrared light source 10, an infrared illumination optical fiber 11 and an illumination lens group 13, and is configured to uniformly illuminate a reference plate alignment mark 41 and the backside alignment mark(s) 20. Moreover, the illumination apparatus 1 can be structurally similar to a Kohler illumination system. In addition, the imaging apparatus 3 may include the backside alignment mark(s) 20, workpiece stage apertures 23, a marble aperture 25, an infrared imaging lens group 31, an infrared reflection mirror 34, an infrared imaging detector 32 and an image processing system 33, and is configured to form clear images of the backside alignment mark(s) 20 and the reference plate alignment mark 41 on a target plane of the infrared imaging detector 32 and calculate positions of these alignment marks.

The present invention also discloses a backside alignment method, comprising: moving the reference plate alignment mark 41 into an imaging field of the imaging apparatus 3 to set up a relationship between position coordinates of the imaging apparatus 3 and the workpiece stage assembly 2; moving each of the backside alignment marks 20 into the imaging field to set up a relationship between position coordinates of the substrate 6 and the imaging apparatus 3; and obtaining the relationship between positions of the substrate 6 and the workpiece stage assembly 2 based on the above two position coordinate relationships.

Figure 6:
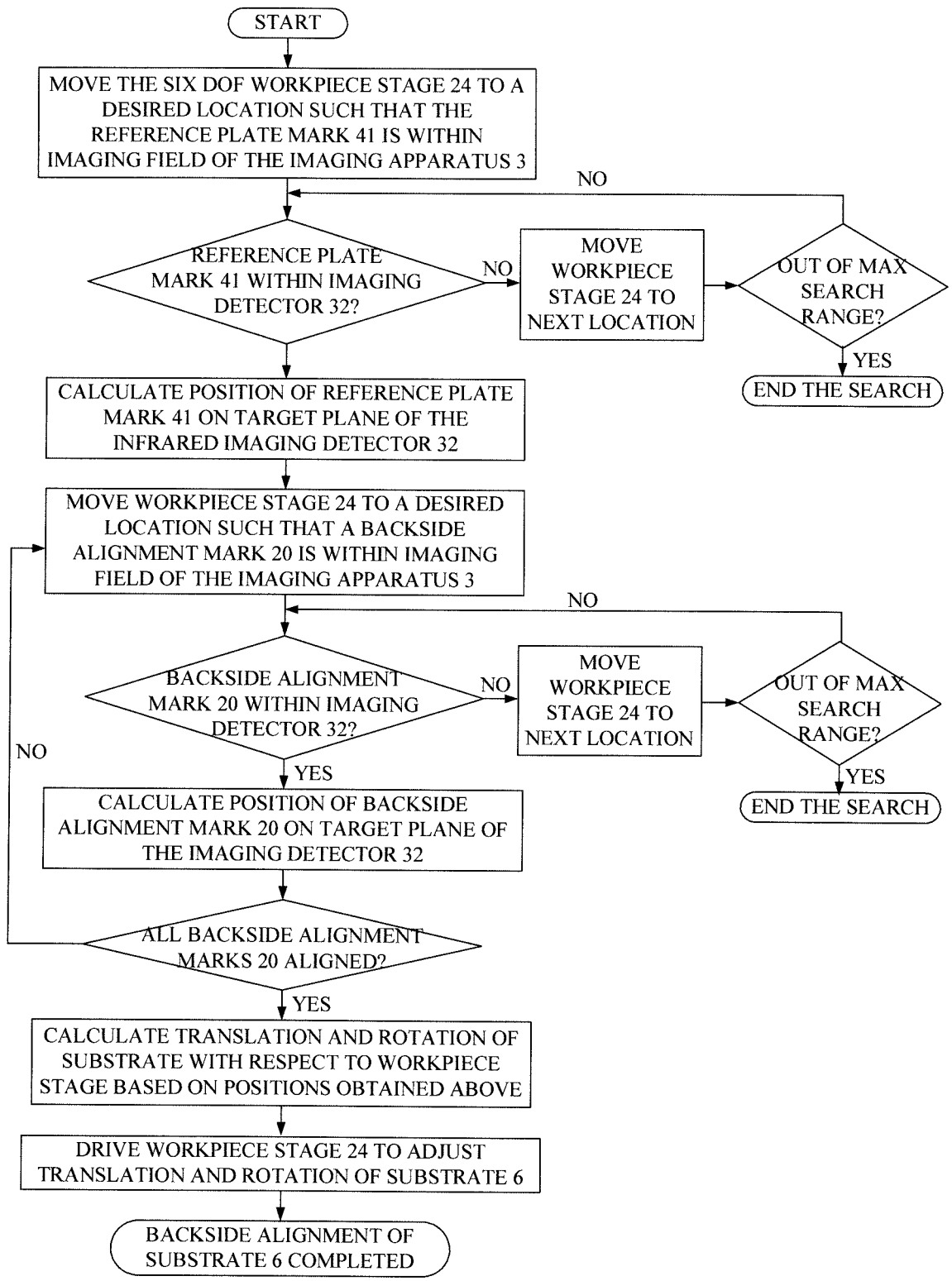
FIG. 6 is a flow chart of a backside alignment method embodying the present invention.

FIG. 6 is a flow chart of this method which may include the steps of:

Step 1: moving the six degree-of-freedom workpiece stage 24 to a desired location such that the reference plate alignment mark 41 is located within an imaging field of the imaging apparatus 3;

Step 2: determining whether the reference plate alignment mark 41 has been captured by the infrared imaging detector 32 using the image processing system 33, and if the reference plate alignment mark 41 is within the imaging detector 32, then calculating a position of the reference plate alignment mark 41 on a target plane of the infrared imaging detector 32 using the image processing system 33 and recording a horizontal position of the workpiece stage 24;

Step 3: if the reference plate alignment mark 41 is not within the infrared imaging detector 32, then moving the workpiece stage 24, by a predetermined distance, into a next search location, if the next search location is out of a predetermined search range, then ending the search; and if the reference plate alignment mark 41 is captured within the predetermined search range, then repeating the step 2;

Step 4: moving the workpiece stage 24 to a desired location such that one of the backside alignment marks 20 is located within an imaging field of the imaging apparatus 3;

Step 5: determining whether the backside alignment mark 20 has been captured by the infrared imaging detector 32 using the image processing system 33, and if the backside alignment mark 20 is within the infrared imaging detector 32, then calculating a position of the backside alignment mark 20 on a target plane of the infrared imaging detector 32 using the image processing system 33 and recording a horizontal position of the workpiece stage 24;

Step 6: if the backside alignment mark 20 is not within the infrared imaging detector 32, then moving the workpiece stage 24, by a predetermined distance, into a next location, if the next search location is out of a predetermined search range, then ending the search; and if the backside alignment mark 20 is captured within the predetermined search range, then repeating the step 5;

Step 7: determining whether all of the backside alignment marks 20 have undergone calculation of their positions on the target plane of the infrared imaging detector 32, if not, then repeating the steps 4, 5 and 6;

Step 8: determining a position relationship between the imaging apparatus 3 and the workpiece stage 24 based on the step 2;

Step 9: determining a position relationship between the substrate 6 and the imaging apparatus 3 based on the steps 5, 6 and 7; and Step 10: determining a position relationship between the substrate 6 and the workpiece stage 24, namely, translation and rotation of the substrate 6 with respect to the workpiece stage 24, based on calculation results of the steps 8 and 9.

As indicated above, the present invention has differences with and advantages over the conventional art as follows: as only one set of illumination apparatus is used, complexity in the design and assembly of illumination apparatus can be reduced and the development costs can be hence lowered; as the illumination apparatus can be disposed within, above or under the marble workpiece stage, coupling between physical interfaces of the illumination apparatus and the workpiece stage assembly can be reduced; also, complexity in the structure design and assembly of the workpiece stage, and processing cost of the workpiece stage can be lowered; and the enabling of moving the workpiece stage to search a backside alignment mark in a certain range when it is not found within an imaging field of the image apparatus can improve the process adaptation of the backside alignment apparatus to the backside alignment marks.

In a word, the apparatuses and methods described in the description are merely several preferable embodiments of the invention which are provided solely for the purpose of describing but not limiting the invention in any way. Any technical solutions which are obtained by those skilled in the art through logical analysis, reasoning or limited experiment in light of the conception of the invention are within the scope as defined in the appended claims.

What is claimed is:

1. A backside alignment apparatus for aligning a substrate having at least one backside alignment mark thereon, the backside alignment apparatus comprising:
    a workpiece stage assembly for supporting the substrate, the workpiece stage assembly including a workpiece stage and a base under the workpiece stage, the workpiece stage being enabled to move in at least three degrees of freedom with respect to the base;
    a reference plate assembly supported by the workpiece stage and including a reference plate alignment mark;
    only one illumination apparatus for emanating an infrared light, the illumination apparatus being disposed on one side of the workpiece stage; and
    only one imaging apparatus disposed on the other side of the workpiece stage and positioned in correspondence with a location of the illumination apparatus, the imaging apparatus having an imaging field,
    wherein the workpiece stage is configured to move the reference plate alignment mark into the imaging field such that the infrared light emanated from the illumination apparatus illuminates and passes through the reference plate alignment mark and the imaging apparatus detects an image of the illuminated reference plate alignment mark,
    wherein the workpiece stage is further configured to move any one of the at least one backside alignment mark into the imaging field such that the infrared light emanated from the illumination apparatus illuminates and passes through said any one of the at least one backside alignment mark and the imaging apparatus detects an image of said any one of the at least one illuminated backside alignment mark.

2. The backside alignment apparatus according to claim 1, wherein the base comprises a base aperture for the infrared light emanated from the illumination apparatus to pass through; the workpiece stage comprises at least two workpiece stage apertures positioned in correspondence with locations of the reference plate alignment mark and the at least one backside alignment mark.

3. The backside alignment apparatus according to claim 2, wherein the illumination apparatus is disposed under the base and comprises an infrared-light source, an optical fiber, an illumination lens group and an illuminating reflection mirror, the infrared light emanated from the infrared-light source successively passing through the optical fiber, the illumination lens group, the illuminating reflection mirror and the base aperture; the imaging apparatus is disposed above the workpiece stage and aligned with the base aperture and comprises from bottom up an imaging lens group, an imaging detector and an image processing system.

4. The backside alignment apparatus according to claim 2, wherein the illumination apparatus is disposed above the workpiece stage and aligned with the base aperture and comprises from top down an infrared-light source, an optical fiber and an illumination lens group, the infrared-light source emanating an infrared light; the imaging apparatus is disposed under the base and comprises an imaging lens group, an illuminating reflection mirror, an imaging detector and an image processing system, the imaging lens group being aligned with the base aperture, the image of the illuminated reference plate alignment mark or any one of the at least one illuminated backside alignment mark successively passing through the imaging lens group, the illuminating reflection mirror and the imaging detector and entering the image processing system.

5. The backside alignment apparatus according to claim 2, wherein the illumination apparatus is disposed within the base aperture and comprises an infrared-light source for emanating an infrared light; the imaging apparatus is disposed above the workpiece stage and aligned with the base aperture and comprises from bottom up an imaging lens group, an imaging detector and an image processing system.

6. The backside alignment apparatus according to claim 3, wherein the image detector is a CCD detector, a CMOS detector, or an InGaAs detector.

7. The backside alignment apparatus according to claim 1, wherein the workpiece stage assembly further comprises a chuck disposed on the workpiece stage, the reference plate assembly and the substrate being held by the chuck, the chuck being formed of glass or a material with a high transmittance for infrared light.

8. The backside alignment apparatus according to claim 1, wherein the reference plate assembly comprises a reference plate and a frame, the reference plate alignment mark being disposed on a bottom surface of the reference plate, the reference plate being fixed on the frame, the reference plate alignment mark leveling with the at least one backside alignment mark.

9. The backside alignment apparatus according to claim 8, wherein the frame is formed of glass or a material with a high transmittance for infrared light.

10. A backside alignment method for determining a relationship between positions of a substrate and a workpiece stage using the backside alignment apparatus according to claim 1, the method comprising:
    a) moving the reference plate alignment mark into an imaging field of the imaging apparatus and acquiring a first position information indicating a relationship between position coordinates of the imaging apparatus and the workpiece stage;
    b) moving each of the at least one backside alignment mark into the imaging field of the imaging apparatus and acquiring a second position information indicating a relationship between position coordinates of the substrate and the imaging apparatus; and
    c) determining a relationship between positions of the substrate and the workpiece stage based on the first and second position information.

11. The backside alignment method according to claim 10, wherein the imaging apparatus comprises an imaging detector and an image processing system, and the step a) comprises:

a1) moving the workpiece stage a predetermined distance, wherein the predetermined distance is expected to locate the reference plate alignment mark is located within an imaging field of the imaging apparatus;

a2) determining, using the image processing system, whether the reference plate alignment mark is within the imaging detector, and if the reference plate alignment mark is within the imaging detector, then calculating a position of the reference plate alignment mark on a target plane of the imaging detector using the image processing system and recording a horizontal position of the workpiece stage; and a3) if the reference plate alignment mark is not within the imaging detector, then moving the workpiece stage, by a predetermined distance, into a next search location; if the next search location is out of a predetermined search range, then ending the search; and if the reference plate alignment mark is captured within the predetermined search range, then repeating the step a2).

12. The backside alignment method according to claim 10, wherein the imaging apparatus comprises an imaging detector and an image processing system, and the step b) comprises:

b1) moving the workpiece stage a predetermined distance, wherein the predetermined distance is expected to locate one of the at least one backside alignment mark is located within an imaging field of the imaging apparatus;

b2) determining, using the image processing system, whether the backside alignment mark is within the imaging detector, and if the backside alignment mark is within the imaging detector, then calculating a position of the backside alignment mark on a target plane of the imaging detector using the image processing system and recording a horizontal position of the workpiece stage;

b3) if the backside alignment mark is not within the imaging detector, then moving the workpiece stage, by a predetermined distance, into a next search location; if the next search location is out of a predetermined search range, then ending the search; and if the backside alignment mark is captured within the predetermined search range, then repeating the step b2); and determining whether positions, on a target plane of the imaging detector, of all of the at least one backside alignment mark have been calculated, if not, then repeating the steps b1), b2) and b3).

\* \* \* \* \*